(12) United States Patent
Naeemi et al.

(10) Patent No.: US 10,328,412 B2
(45) Date of Patent: Jun. 25, 2019

(54) HYDROGEN STORAGE SYSTEM BY CATALYTIC DEHYDROGENATION OF AMINES

(71) Applicant: ASEMBLON INC., Woodinville, WA (US)

(72) Inventors: Esmaeel Naeemi, Woodinville, WA (US); David G. O'Connor, Woodinville, WA (US); Maitham Naeemi, Woodnville, WA (US)

( * ) Notice: Subject to any disclaimer, the term of this patent is extended or adjusted under 35 U.S.C. 154(b) by 1334 days.

(21) Appl. No.: 14/157,123

(22) Filed: Jan. 16, 2014

(65) Prior Publication Data

US 2014/0134100 A1    May 15, 2014

Related U.S. Application Data

(63) Continuation-in-part of application No. 12/707,658, filed on Feb. 17, 2010, now abandoned.

(51) Int. Cl.
*B01J 19/18* (2006.01)
*B01J 8/00* (2006.01)
(Continued)

(52) U.S. Cl.
CPC ........... *B01J 19/1893* (2013.01); *B01J 8/009* (2013.01); *B01J 8/0214* (2013.01); *B01J 8/0221* (2013.01);
(Continued)

(58) Field of Classification Search
CPC ...... B01J 19/1893; B01J 19/249; B01J 8/009; B01J 8/0214; B01J 8/0221; C01B 3/22; C01B 3/501; C07C 253/00
(Continued)

(56) References Cited

U.S. PATENT DOCUMENTS

2,388,218 A * 10/1945 Olin ..................... C07C 253/00
558/308
3,679,773 A * 7/1972 Kovach ................... C07C 5/325
208/145
(Continued)

*Primary Examiner* — Huy Tram Nguyen
(74) *Attorney, Agent, or Firm* — Olympic Patent Works PLLC (57) ABSTRACT

The current disclosure is directed to a hydrogen-storage system that employs catalytic dehydrogenation of low-molecular-weight amines in a hydrogen reactor. The hydrogen-storage system comprises aliphatic amines and di-amines as organic carriers that store hydrogen covalently, a hydrogen reactor that releases and separates hydrogen gas from the carrier, and metal or metal-oxide catalysts that promote a dehydrogenation reaction to release hydrogen. In certain implementations, a metal or metal-oxide catalyst may be carried on high-surface-area support materials, such as gamma-alumina and metal-organic-framework materials, to enhance catalytic properties. The hydrogen reactor may be a packed-bed reactor, a monolith reactor, or a flow-through hydrogen-membrane reactor. In one implementation, the flow-through hydrogen-membrane reactor comprises an inlet through which the organic hydrogen carrier flows into the reactor, a hydrogen-separation membrane selectively permeable to hydrogen, a recirulation outlet for removing unspent organic carrier, and a hydrogen outlet for releasing hydrogen and reaction byproducts. The spent organic carrier are collected and hydrogenated to regenerate the original fuel.

20 Claims, 4 Drawing Sheets

(51) Int. Cl.
 *C01B 3/22* (2006.01)
 *C07C 253/00* (2006.01)
 *B01J 19/24* (2006.01)
 *B01J 8/02* (2006.01)
 *C01B 3/50* (2006.01)

(52) U.S. Cl.
 CPC ............... *B01J 19/249* (2013.01); *C01B 3/22* (2013.01); *C01B 3/501* (2013.01); *C07C 253/00* (2013.01); *B01J 2208/00053* (2013.01); *B01J 2208/00407* (2013.01); *B01J 2208/00415* (2013.01); *C01B 2203/0277* (2013.01); *C01B 2203/041* (2013.01); *C01B 2203/048* (2013.01); *C01B 2203/066* (2013.01); *C01B 2203/107* (2013.01); *C01B 2203/1047* (2013.01); *C01B 2203/1052* (2013.01); *C01B 2203/1058* (2013.01); *C01B 2203/1064* (2013.01)

(58) Field of Classification Search
 USPC .......................................................... 422/221
 See application file for complete search history.

(56) References Cited

U.S. PATENT DOCUMENTS

| | | | | |
|---|---|---|---|---|
| 4,197,081 | A * | 4/1980 | Osborg | C10L 1/00 431/2 |
| 5,888,273 | A * | 3/1999 | Buxbaum | B01D 53/22 95/45 |
| 6,476,267 | B1 * | 11/2002 | Fuchigami | C07C 209/48 546/329 |
| 6,680,042 | B1 * | 1/2004 | Schulz | C01B 3/0005 423/644 |
| 6,919,062 | B1 * | 7/2005 | Vasileiadis | C07C 29/1518 423/437.1 |
| 7,285,142 | B1 * | 10/2007 | Mohajeri | B01J 7/02 423/648.1 |
| 2004/0223907 | A1 * | 11/2004 | Pez | C01B 3/0015 423/648.1 |
| 2007/0082811 | A1 * | 4/2007 | Soled | B01J 23/8871 502/302 |
| 2008/0260630 | A1 * | 10/2008 | Pez | C01B 3/22 423/651 |
| 2009/0246575 | A1 * | 10/2009 | Zhao | B01J 31/121 429/421 |

* cited by examiner

HYDROGEN STORAGE SYSTEM BY CATALYTIC DEHYDROGENATION OF AMINES

CROSS-REFERENCE TO RELATED APPLICATION

This is a continuation-in-part of application Ser. No. 12/707,658 filed on Feb. 17, 2010.

TECHNICAL FIELD

This current application is related to a hydrogen storage system and, in particular, to a system for hydrogen storage and release by catalytic dehydrogenation of aliphatic amines and di-amines.

BACKGROUND

Hydrogen storage is a technical barrier that currently inhibits widespread use of hydrogen as an energy carrier. While many methods for hydrogen storage have been proposed, such as compressed hydrogen, metal hydrides, cryogenic hydrogen, organic liquid hydrogen carriers, and chemical hybrids, each method has drawbacks. Organic liquid hydrogen carriers represent an attractive technology. Organic liquid hydrogen carriers undergo reversible hydrogenation and dehydrogenation to store and release hydrogen gas. However, dehydrogenation reactions are thermodynamically unfavorable, are therefore generally conducted at elevated temperatures and in the presence of catalysts, and are commonly associated with various undesired side reactions. Development of a thermodynamically balanced hydrogenation/dehydrogenation system for hydrogen storage and release is one challenge that many researchers and developers seek to meet in the course of establishing a hydrogen-base economy.

SUMMARY

The current disclosure is directed to a hydrogen-storage system that employs catalytic dehydrogenation of low-molecular-weight amines in a hydrogen reactor. The hydrogen-storage system comprises aliphatic amines and di-amines as organic carriers that store hydrogen covalently, a hydrogen reactor that releases and separates hydrogen gas from the carrier, and metal or metal-oxide catalysts that promote a dehydrogenation reaction to release hydrogen. In certain implementations, a metal or metal-oxide catalyst may be carried on high-surface-area support materials, such as gamma-alumina and metal-organic-framework materials, to enhance catalytic properties. The hydrogen reactor may be a packed-bed reactor, a monolith reactor, or a flow-through hydrogen-membrane reactor. In one implementation, the flow-through hydrogen-membrane reactor comprises an inlet through which the organic hydrogen carrier flows into the reactor, a hydrogen-separation membrane selectively permeable to hydrogen, a recirulation outlet for removing unspent organic carrier, and a hydrogen outlet for releasing hydrogen and reaction byproducts. The spent organic carrier are collected and hydrogenated to regenerate the original fuel.

DETAILED DESCRIPTION

The current document discloses a system that chemically stores hydrogen in low-molecular-weight amines and that releases hydrogen by dehydrogenating the low-molecular-weight amines to corresponding nitriles in a catalytic reactor. In the following discussion, aliphatic amines and di-amines are first introduced, in a first subsection, as liquid organic hydrogen carriers. A second subsection discusses metal and metal-oxide catalysts carried on various support materials. A third subsection discusses catalytic dehydrogenation reactions for releasing hydrogen gas from aliphatic amines in various types of hydrogen reactors. A fourth subsection describes a design for a hydrogen-membrane-reactor system. A fifth subsection discusses hydrogen-selective membranes that may be used in various types of hydrogen-membrane reactors.

Aliphatic Amines and Di-amines as Liquid Organic Hydrogen Carrier

Organic liquid hydrogen carriers are considered to be commercially viable materials for hydrogen storage within vehicles. Certain hydrogen-containing organic compounds can form an unsaturated bond via a dehydrogenation reaction and, at the same time, reversibly release hydrogen. Organic liquid carriers have certain advantages with respect to other hydrogen storage methods, including utilization of the existing liquid-fuel infrastructure, high energy efficiency, and good safety characteristics. Desirable characteristics of organic hydrogen carriers include: (1) facile, clean and reversible dehydrogenation; (2) an enthalpy of dehydrogenation low enough that dehydrogenation is thermodynamically favored at mild temperatures, at least below 180° C.; (3) a liquid state; (4) nonvolatility from −40° C. to the dehydrogenation temperature; (5) a hydrogen storage capacity of at least greater than 6% by weight and 45 g $H_2$ per liter of liquid; and (6) stability with respect to thermal or catalytic decomposition at operating temperatures. It is desirable that release of hydrogen is reversible so that the organic hydrogen carriers can again store hydrogen, via a hydrogenation reaction, in subsequent hydrogen-storage-and-hydrogen-release cycles.

Amines, for example, aliphatic amines and di-amines, have been identified as promising, high-capacity chemical hydrogen carriers. Aliphatic amines and di-amines contain hydrogen covalently bonded to carbon and nitrogen atoms that can be released by catalytic dehydrogenation reactions. These organic compounds can theoretically store 6.7 to 13.6 wt. % of releasable hydrogen. The general amine-to-nitrile dehydrogenation reaction is represented by the following equation:

$$RCH_2NH_2 \longleftrightarrow RCN + 2H_2$$
amine  nitrile where R is any aliphatic or cyclo-aliphatic moiety. R may be a methyl group, in which case the product of the reaction is acetonitrile and hydrogen. Dehydrogenation of amines to nitriles has been carried out with a variety of reagents to improve reaction rates and lower the activation energy so that they become economically feasible in industrial applications. Stoichiometric metal oxidants, such as manganese dioxide, silver oxide, nickel peroxide, NaOCl in micelles, $K_2S_2O_8$—$NiSO_4$, and CuCl—$O_2$-pyridine are generally used for this purpose. However, many drawbacks have been encountered in using these reagents, including low yields, unsatisfactory product selectivity, harsh reaction conditions, large amounts of toxic byproducts, tedious preparation procedures, and other limitations. Dehydrogenation reactions are also commonly associated with various side reactions, such as deamination, formation of hydrogen cyanide, rehydrogenation of nitriles back to amines, and decomposition of amines and nitriles. In particular, the desired product from these reactions has been the nitrite, not the hydrogen gas, so the hydrogen is usually eliminated by adding an oxidant as the hydrogen receptor. Thus, although amines represent a promising candidate for organic hydrogen carrier, conventional methods of oxidizing amines to form nitriles cannot be used to release and collect hydrogen gas. The current disclosure provides a solution for developing a reversible hydrogenation/dehydrogenation system employing aliphatic amines and di-amines as high-capacity organic hydrogen carriers for efficient hydrogen storage and release.

Figure 1:
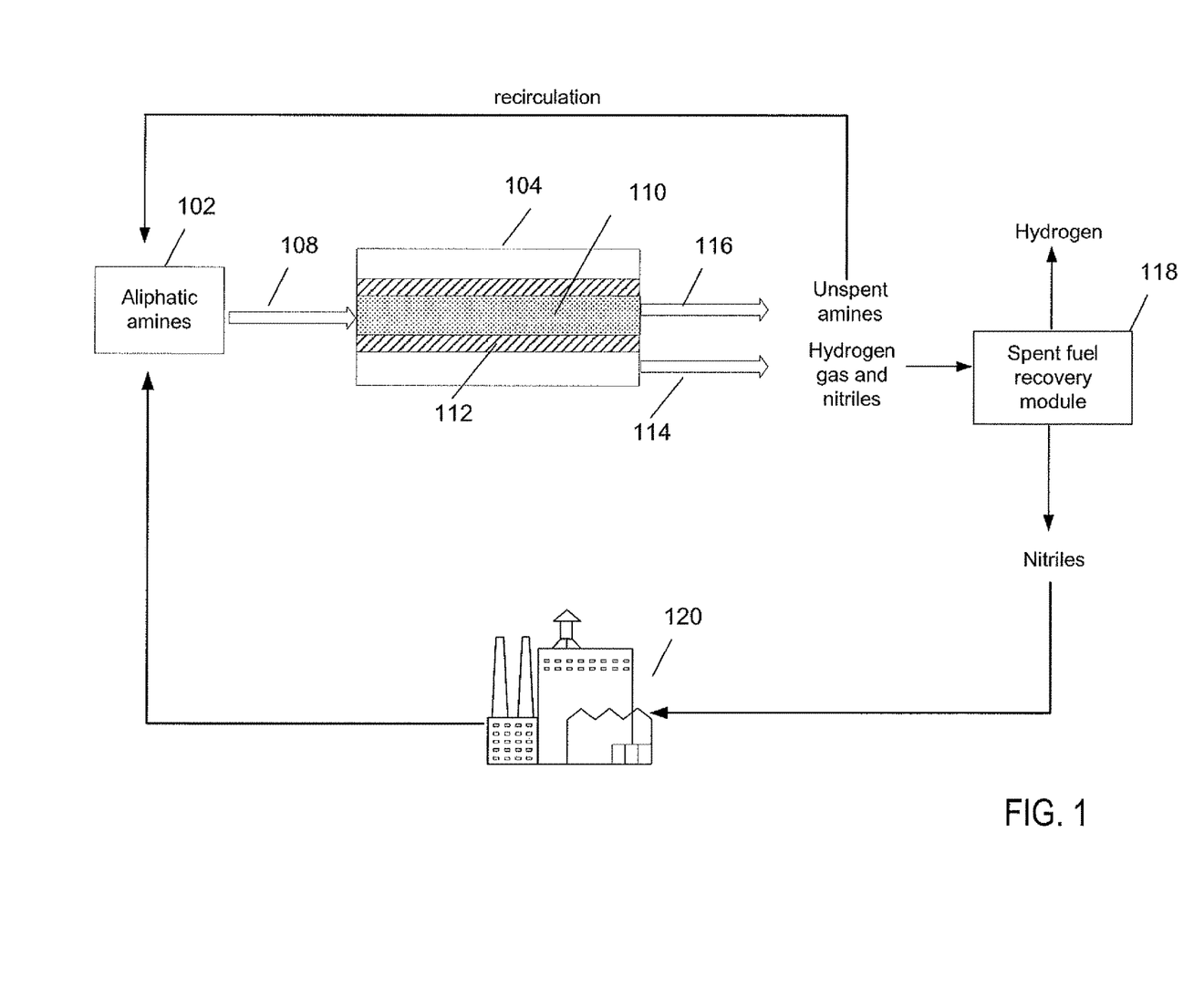
FIG. 1 shows a schematic overview of a hydrogen-storage system that uses amines as organic liquid carriers.

FIG. 1 shows a schematic overview of a hydrogen-storage system that uses amines as organic liquid carriers. Aliphatic amines 102 are input into a hydrogen reactor 104 for dehydrogenation and release of hydrogen. Hydrogen reactors enhance hydrogen production and facilitate separation of hydrogen from other gases. The catalytic dehydrogenation reaction takes place in an inner chamber of the hydrogen reactor 110 that is generally filled with metal catalysts. Hydrogen generated by the dehydrogenation reaction is removed from the reaction mixture as fast as it is produced in order to minimize contact time and prevent the reverse hydrogenation reaction. In the case of a membrane reactor 104, a hydrogen-selective membrane 112 with high permeability and selectivity for hydrogen may be used. The hydrogen-membrane reactor may comprise an inlet 108 through which an organic hydrogen carrier can flow into the reactor, a recirculation outlet 116 for removing the unspent organic carrier, and a hydrogen outlet 114 for releasing hydrogen gas and reaction byproducts, such as spent organic carrier in the form of various nitriles.

The unspent amines are recirculated back into the hydrogen reactor for dehydrogenation. The dehydrogenated organic carrier, nitriles in this case, and hydrogen gas are further processed in a spent fuel recovery module 118 where they are separated by their physical properties. The separated hydrogen gas is then directed to power hydrogen consuming devices, such as internal combustion engines, turbines, or fuel cells. The dehydrogenated organic carrier from the spent fuel recovery module 118 may be directed to a dual-bladder gas tank either on-board a vehicle or at a stationary site, where the dehydrogenated organic carrier is stored until it can be removed and transported to a hydrogenation plant 120 at a remote site for catalytic hydrogenation. In the hydrogenation plant 120, the dehydrogenated organic carrier is hydrogenated to regenerate the original organic carrier by reacting with hydrogen. The hydrogen utilized for regenerating the original organic carrier from the dehydrogenated organic carrier can be obtained by various methods for hydrogen generation, for example, conventional hydrogen production methods of steam methane reforming and grid-powered electrolysis.

Metal and Metal Oxide Catalysts

Oxides and metal catalysts are used in the catalytic dehydrogenation of amines to corresponding nitriles in order to minimize side-reaction activity and improve conversion to, and selectivity for, desired products. Common catalysts for dehydrogenation reactions include Group VIII metals, alloys, and/or combinations of these catalysts. Various noble metals have shown to have useful catalytic activities, including Rh, Pt, Ru, Au or Pd, either mixed or in pure form, and either granulated or anchored on high-surface-area substrate. Effective catalysts generally have a long life-span. In the current disclosure, the catalytic dehydrogenation process has been tested, in various reactor configurations, with several candidate catalysts, including cobalt, cobalt (II) oxide, cobalt (III) oxide, iron (II) oxide, iron (III) oxide, chromium oxide, and nickel oxide.

Commercial metal or metal-oxide catalysts were purchased from Sigma-Aldrich. Metal-oxide catalysts may also be made from metal powder using microwave-heating technology. In one implementation, to prepare the cobalt oxide using a microwave, about 5 grams of cobalt metal powder was placed in a ceramic crucible and heated in a microwave oven for 3 minutes. The power of the microwave was set to 950 W. Upon generation of microwave radiation, the cobalt metal powder started to glow red-hot within a minute. The microwave heating of the sample was continued for 3 minutes. After completion, the sample was crushed and used without further treatment. Samples were analyzed by Gas Chromatography/Mass Spectrometry (GC/MS), for example, an Hewlett-Packard GC/MS system 5890-5972A equipped with a 0.25 mm I.D. (inner diameter)×30 m fused-silica capillary column.

Most industrial catalysts contain a small amount of the active components dispersed over high-surface-area supports. The choice of the support depends on several factors, including the stability of the catalyst in the reaction medium, the nature of the porous structure, surface area, and other factors. Different types of high-surface-area supports may be used for the preparation of the catalysts, including silica, activated carbon, gamma-alumina, metal-organic frameworks, and other support materials. The choice of the support may be a significant design parameter in designing a supported catalyst with desired activity and selectivity. Gamma-alumina (γ-alumina) is commonly used as a support material for dehydrogenation catalysts because of its high surface area and capacity to maintain high metal dispersions even at high temperature. The large pore volume of this material allows reactant molecules to penetrate rapidly and uniformly to catalytic sites. Thus, γ-alumina is one of the most widely used catalyst supports for commercial catalytic applications, and may be used as support for metal and metal oxide catalysts in the currently disclosed hydrogen reactor systems.

Metal-organic frameworks ("MOFs") may also be used for the stabilization and support of metal catalysts and often offer improved catalyst efficiency compared to catalysts in pelletized form, for example, in a packed-bed reactor or in a monolith reactor, due to the greatly increased internal surface area and well defined pore structures provided by MOFs. MOFs are microporous materials synthesized by assembling metal ions with organic ligands. MOFs typically have crystalline structures and are characterized by large internal surface areas and cavities of tunable size. It is believed that the crystalline porous structures of MOFs may maintain the stability of the catalyst and limit the migration and agglomeration of small metal particles, increasing the number of catalytic sites of the catalyst. MOF supported catalysts may be prepared by embedding naked catalysts within the cavities of MOFs. Alternatively, metal catalysts may be first stabilized with certain surfactants or capping agents and then encapsulated by MOFs in case that their hydrodynamic radius is larger than the cavity size of the MOF.

Catalytic Dehydrogenation Reactions in Various Types of Hydrogen Reactors

Propylamine was used to investigate the catalytic properties of various types of catalysts. Propylamine is a liquid at room temperature. The dehydrogenation reaction, shown below, produces two moles of hydrogen gas by oxidizing propylamine to propionitrile.

$$CH_3CH_2CH_2NH_2 \longleftrightarrow CH_3CH_2CN + 2H_2$$

propylamine                           propionitrile

The ratio of propionitrile to propylamine can be easily quantified in a GC/MS instrument.

Various hydrogen reactor setups, including packed-bed reactors, monolith reactors, and membrane reactors, were used to test the dehydrogenation reactions of propylamine to propylamine and the catalytic efficiency of various catalysts. In one test, a small packed-bed reactor was used for initial catalyst screening. The small packed-bed reactor contained about 0.5 g of a catalyst candidate packed into a glass tube with an inner diameter of 0.93 mm. The packed-bed reactor was placed in a controllable, heated housing under a constant flow of sweep gas, for example, helium, at 10 psig (pounds per square inch gauge). The gases employed in various hydrogen reactors were purchased from Airgas, including grade 5 $H_2$, He, $N_2$, and ultra high purity (UHP) grade $O_2$. with a purity percentage of 99.99%. The heated housing was adjusted to various temperatures, ranging from about 200° C. to about 300° C. At each temperature, 0.1 μl of propylamine was injected into the inlet of the glass tube, where it was carried through the reactor by the helium sweep gas, flowing at a range of 1-2 ml/min, depending on the packing of the catalyst. The exit stream of the reactor was connected to the GC/MS, where it was analyzed for the reactant material, propionitirle, and any other byproducts.

The results were analyzed by, for example, calculating the ratio of the area of the propionitrile peak to the total area of other compounds. This provides an approximate percent conversion. The number of peaks other than propylamine and propionitrile were used to give a high-, medium-, or low-selectivity label to each run. A high-selectivity label indicates that only propionitrile and propylamine were observed. A medium-selectivity label indicates detection of up to two additional byproducts. A low-selectivity label indicates detection of more than two additional byproducts. Of all the candidates tested, only a few were selected for further testing in a larger packed bed reactor. Table 1 lists the screening results of the catalysts selected for further testing.

TABLE 1

Screening results of the catalysts selected for further testing

|  | 200° C. | 250° C. | 280° C. | 300° C. |
|---|---|---|---|---|
| Cobalt |  |  |  |  |
| Conversion | No Conversion | No Conversion | 63% | 78% |
| Selectivity | No Conversion | No Conversion | Medium | High |
| Cobalt Oxide |  |  |  |  |
| Conversion | No Conversion | No Conversion | No Conversion | 47% |
| Selectivity | No Conversion | No Conversion | No Conversion | Medium |
| Cobalt Oxide Micro |  |  |  |  |
| Conversion | 7% | 72% | 72% | 67% |
| Selectivity | High | Medium | High | Medium |
| Nickel |  |  |  |  |
| Conversion | 40% | 60% | 65% | 60% |
| Selectivity | High | High | Medium | Low |

Cobalt, cobalt oxide and nickel all showed promising results as catalysts for the dehydrogenation reaction in the screening process. Cobalt oxide was tested in two forms, the commercially available cobalt oxide purchased from Sigma-Aldrich and the microwave cobalt oxide described above. As for the catalysts that did not pass the initial screening process, including copper, chromium, iron, and their oxides, the results indicated either low overall activity or, in the case of copper, high activity but extremely low selectivity.

After the screening process, the catalysts listed in Table I were further tested in a larger packed-bed reactor. In one implementation, the larger packed-bed reactor was set up by packing 0.5 gm of a catalyst in a tube of ¼ inch inner diameter with glass wool at both ends of the catalyst. Each catalyst was heated to a specified reaction temperature. The temperature at the catalyst surface was measured by a thermocouple and controlled by a temperature controller. Propylamine was delivered to the reactor by a dual-piston pump that controlled inlet volumetric flow rate. Propylamine was vaporized prior to entering the reactor and the vapor temperature was controlled to a predetermined catalyst temperature. The product stream exiting the reactor was condensed to room temperature using ice cold water. The inlet stream and product stream were analyzed by GC/MS to calculate conversion ratio. A qualitative hydrogen-gas detector was incorporated in the exit stream, allowing for a direct observation of hydrogen gas formation in addition to the observation of propionitrile production. The reactivity of each catalyst was measured at various temperatures. The temperature of reaction was varied from about 250° C. to about 350° C. The inlet flow rate was 0.125 ml/min, corresponding to a space velocity of 4181 ml/hr/g of the catalyst. The space velocity was defined as the inlet gas volumetric flow rate divided by the weight of the catalyst.

Figure 2:
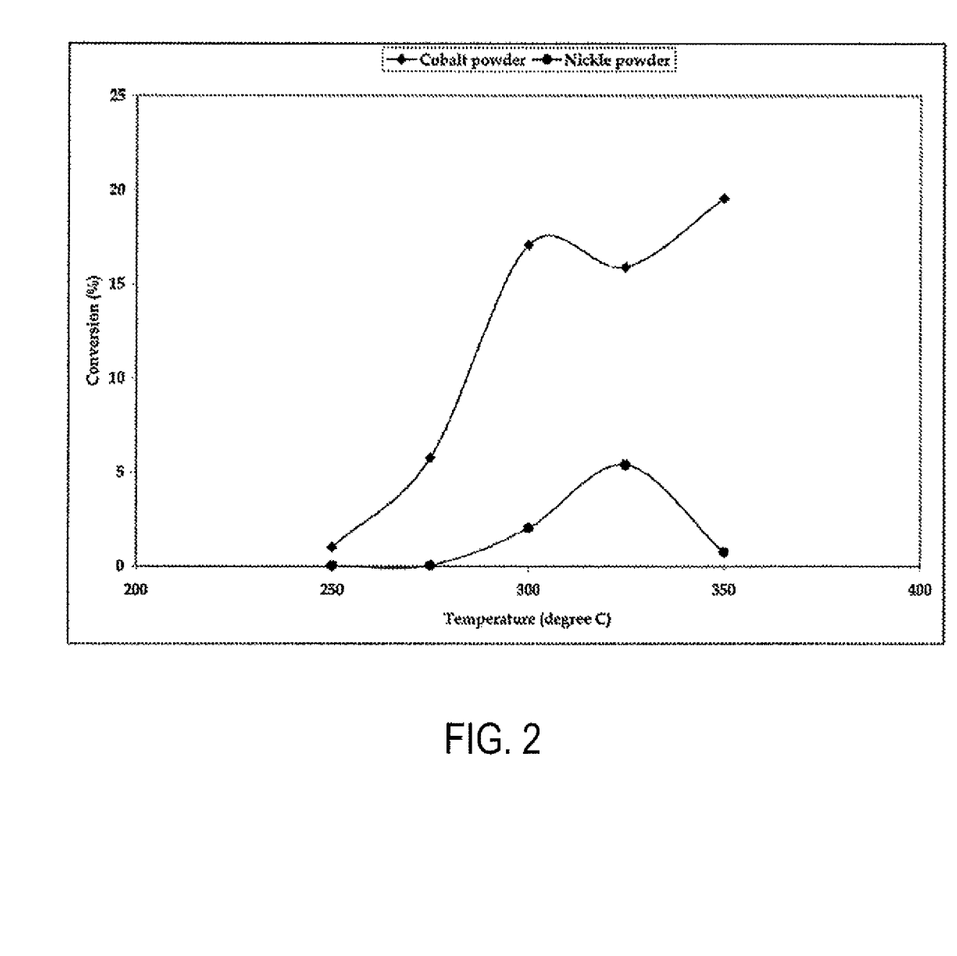
FIG. 2 shows conversion-versus-temperature curves for commercial cobalt and nickel catalysts tested in the larger packed-bed reactor.

FIG. 2 shows conversion-versus-temperature curves for commercial cobalt and nickel catalysts tested in the larger packed-bed reactor. The conversion ratio was calculated by dividing the amount of propionitrile in the product stream by the amount of propylamine in the inlet stream. Apparent activation energies were calculated from these results as 129 kJ/mol and 215 kJ/mol for commercial cobalt and nickel particles, respectively.

Two forms of cobalt oxides were determined to be effective in the larger packed-bed reactor. Nickel showed high conversion and selectivity at relatively mild temperatures, such as approximately 250° C., during the screening process, but performed poorly in the larger packed-bed reactor where selectivity drops significantly. In the larger packed-bed reactor, no propylamine or propionitrile was detected, while many other side products were detected. While this may be due to a number of factors, one factor may be that nickel has a high affinity for hydrogen and may absorb the hydrogen gas produced by the dehydrogenation reaction, leading to catalysis of many other side reactions. In the screening process, the glass tube setup required continuous flow of a helium sweep gas through the catalyst, carrying the injected propylamine and all reaction products through the reactor. But, in the larger packed-bed reactor, the helium gas was replaced with a hydrogen sweep gas, so that the hydrogen was constantly available to interfere with the reactions and initiates side reactions. Since nickel may also be used as a hydrogenation catalyst, the presence of hydrogen gas changes nickel's catalytic activity and favors the reverse hydrogenation reaction that converts propionitriles back to propylamines. Thus, removal of hydrogen as soon as it is formed is desirable for efficient hydrogen recovery.

Since cobalt oxides performed well both in the initial screening process and in the larger packed-bed reactor, a larger monolith reactor was used to further test their catalytic efficiency. In one implementation, the larger monolith reactor was set up by depositing cobalt oxide on the monolith by wash coating with 3-5% by weight loading. This reactor consisted of an 18-inch-long stainless steel, tubular housing with a 4.5 inch inner diameter, containing two 900 cpsi (cells per square inch) and two 1000 cpsi monoliths. The reactor was heated by a series of band heaters wrapped around the outside of the reactor housing, while the temperature was controlled based on a series of thermocouples set inside the reactor. A pump was used to push the liquid fuel, for example, propylamine, through a series of vaporizers from a reservoir into the reactor. A first vaporizer was used to vaporize the liquid fuel, while a second vaporizer was used to heat the fuel vapor to the same temperature as that of the catalyst. The vapor exiting from the reactor was passed through a heat exchanger, lowering the overall temperature of the exiting stream to approximately 30° C. At this point, the mixture of vapor and liquids was passed through a separator. In one implementation, the separator was a 2 liter closed container that had a ¼ inch liquid outlet at the lower part that returned the liquid back to the reservoir and a ¼ inch gas outlet on the top to remove the vapors. The vapors then passed into a series of scrubbers which removed all traces of organic compounds from the produced hydrogen gas. The purified stream of hydrogen gas was then passed through a qualitative hydrogen detector and a mass flow meter. In one experiment, the hydrogen detector indicated ~100% purity of the hydrogen gas produced by the dehydrogenation reaction and a mass flow meter indicated ~4.3 L/min of gas flow. The hydrogen gas may be directly fed into a hydrogen vehicle, for example, a 4-stroke Honda engine with a 25 cc displacement, modified to run on hydrogen gas.

Design of a Hydrogen-membrane Reactor

In membrane reactors commonly used in dehydrogenation reactions, for example, dehydrogenation of amines to nitriles, hydrogen gas produced by dehydrogenation passes through a hydrogen-selective membrane. The removal of hydrogen gas from the reactor raises the conversion ratio for the dehydrogenation reaction, rendering the process more economical. One implementation of a hydrogen-membrane reactor device is shown in greater detail in FIGS. 3 and 4.

Figure 3:
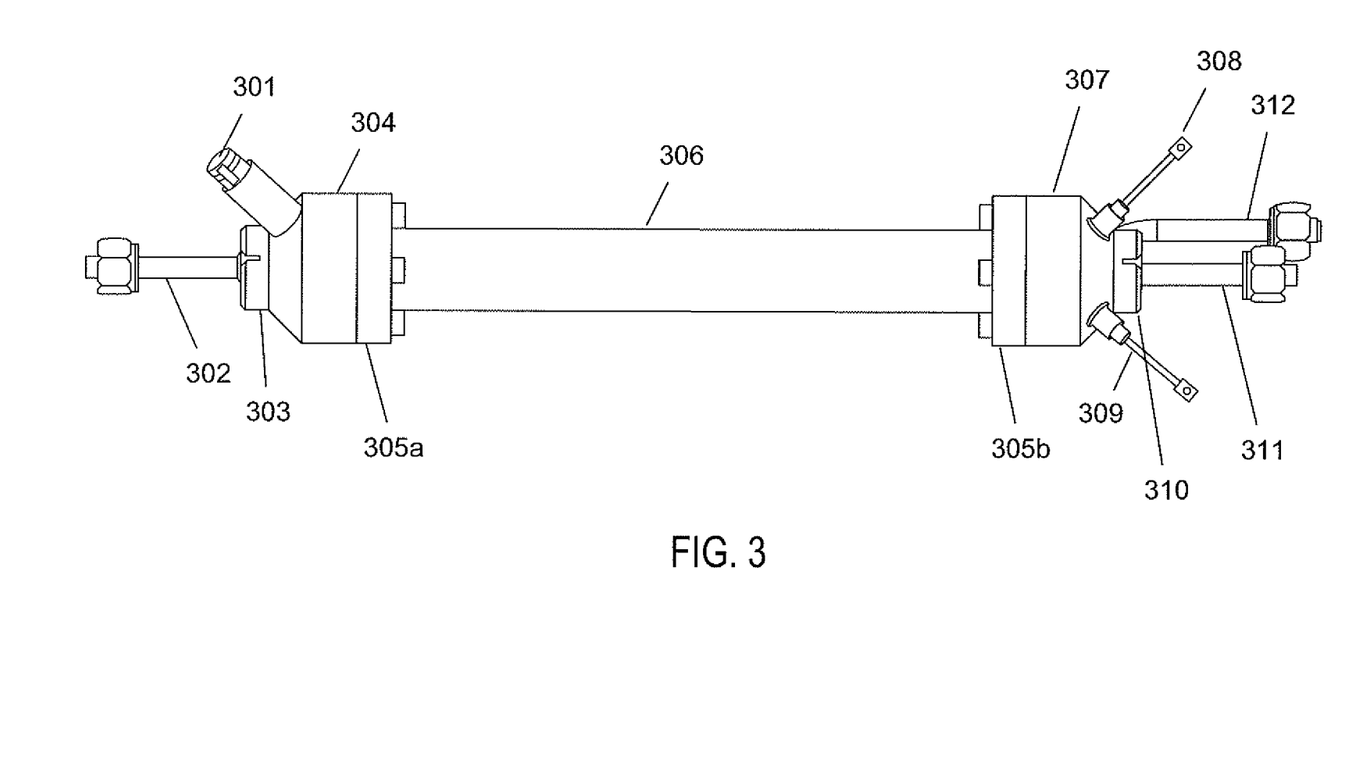
FIG. 3 shows an external view of a prototype hydrogen-membrane reactor.

FIG. 3 shows an external view of a prototype hydrogen-membrane reactor. In FIG. 3, power is introduced into the reactor through a power input connector 301 to provide current to a plurality of heaters. Vaporized fuel, for example, primary amines, flows into the reactor through a vapor-fuel inlet tube 302. An inlet cap flange 303 holds the vapor-fuel inlet tube 302 to an inlet tube cap 304 and the inlet-cap flange 303 seals the vapor-fuel inlet tube 302 using, for example, an O-ring. Two cap flange clamps 305a and 305b on the inlet and outlet side of the reactor, respectively, hold the outer reactor tube 306 to the inlet cap flange 303 and a recirculation outlet flange 310. The outer reactor tube 306 defines the length of the reactor in addition to providing a chamber for capturing hydrogen. On the outlet side, a positive thermocouple feed-through 308, a negative thermocouple feed-through 309, and a hydrogen outlet tube 312 are arranged on an outlet tube cap 307. The positive and negative thermocouple feed-throughs provide electrical connection to a positive lead and a negative lead of one or more thermocouples inside the reactor. A recirculation outlet flange 310 holds a recirculation outlet tube 311 to the outlet tube cap 307. The recirculation outlet flange 310 also provides sealing, using, for example, an O-ring. The recirculation outlet tube 311 removes un-reacted fuel from the reactor. Hydrogen gas and reaction byproducts, such as spent fuel in the form of various nitrites, exit the reactor through the hydrogen outlet tube 312.

Figure 4:
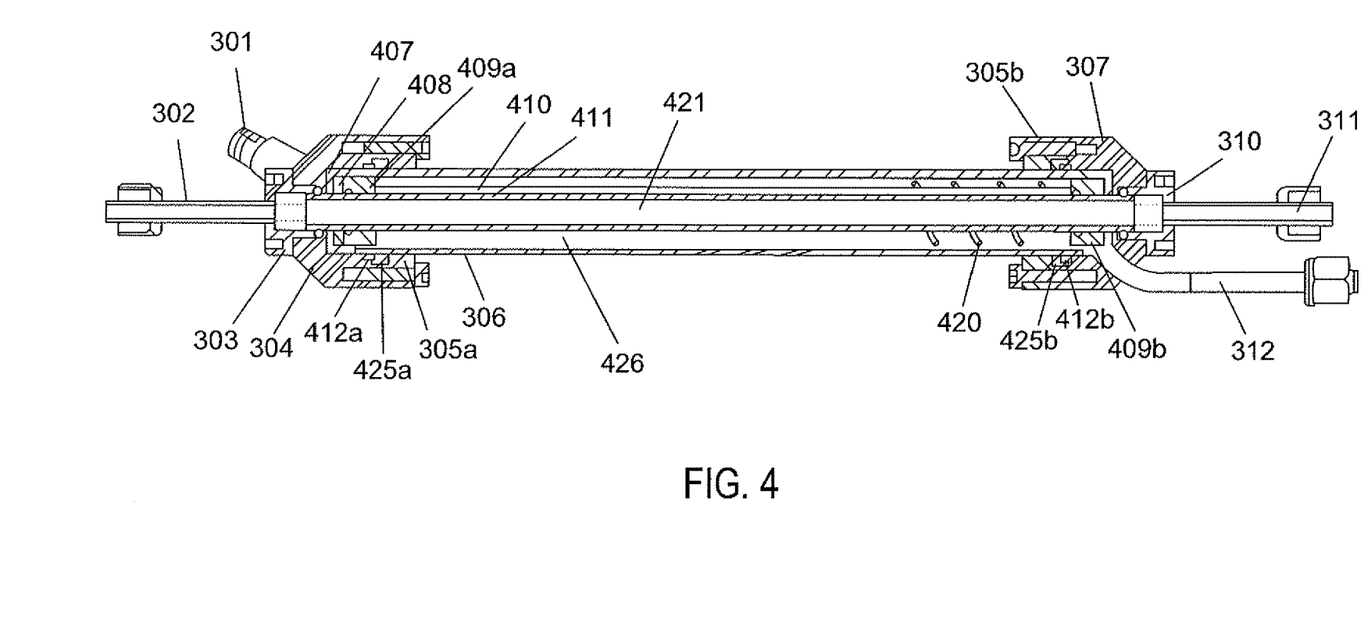
FIG. 4 shows a cross-sectional view of the hydrogen-membrane reactor.

FIG. 4 shows a cross-sectional view of the hydrogen-membrane reactor. The inlet tube 302 provides an input to the reactor through the inlet-cap flange 303. The recirculation outlet tube 311 provides an exit port through the recirculation outlet cap flange 310. Outer reactor tube flanges 425a and 425b are coupled to the outer reactor tube 306 to form a gas-tight seal a few millimeters from the ends of the outer reactor tube 306. Cap flange clamps 305a and 305b are used to clamp against the outer reactor tube flanges 425a and 425b and seal, with O-rings 412, to the inlet tube cap 304 and the outlet tube cap 307. A membrane reactor tube 411 is positioned along the center of the outer reactor tube 306 so that the ends of the membrane reactor tube 411 are approximately equal distance from the ends of both the inlet tube cap 304 and the outlet tube cap 307. The membrane reactor tube 411 is held in place and sealed to the reactor with O-rings. The O-ring and membrane reactor tube 411 are clamped and sealed at the inlet end of the reactor by the inlet cap flange 303. The O-ring and the membrane reactor tube are clamped and sealed at the outlet end of the reactor by the recirculation outlet flange 310.

The outer diameter of power connector 301 is coupled to the inlet tube cap 304 to form a gas tight seal. The center electrode of the power connector 301 passes through an insulator 407 and couples to an input power electrode 408. Heater electrodes 409a and 409b are positioned at equal distances from the ends of the membrane reactor tube 411. Graphite carbon rods 410 are placed around the outside perimeter of the membrane reactor tube 411 so that the outside circumference of the membrane reactor tube 411 and the graphite carbon rods 410 touch one another. The heater electrodes 409a and 409b secure the graphite carbon rods 410 in place and provide electrical contact to the rods. The rods are secured to the heater electrodes 409a and 409b with set screws on either end of the graphite carbon rod 410. Electrical connection to the heater electrodes is provided by connecting one end of the outlet tube cap 307 to an end of the heater electrode 409b by a screw and connecting the other end of the inlet tube cap 304 to the input power electrode 408 by a screw. Heater temperature is monitored through a thermocouple 420. The positive lead of the thermocouple 420 is connected to the positive thermocouple feed-through 308. The negative lead of the thermocouple 420 is connected to the negative thermocouple feed-through 309. The thermocouple 420 is secured to the outer circumference of the membrane reactor tube 411 at a point approximately at the middle of its length between the graphite carbon rods 410.

Vaporized fuel enters the reactor through tube 302 and passes through the inlet cap flange 303 and then into the active reactor volume 421 filled with catalysts, where the vapor comes in contact with the inner surface of the reactor membrane tube 411. The catalytic dehydrogenation reactions take place in the active reactor volume 421. Hydrogen gas and spent fuel pass through a hydrogen membrane within the tube wall and into a space 426 between the reactor membrane tube 411 and the inner wall of the outer reactor tube 306. The difference in the hydrogen partial pressures between the reaction side and the permeate side is the driving force for hydrogen permeation. Since the elevated pressure in the reactor volume provides an adequate transmembrane driving force for permeation of hydrogen, neither a vacuum pump nor sweep gas is needed in the reactor. Hydrogen and reaction byproducts, such as spent fuel in the form of various nitriles, then exit the reactor through the hydrogen outlet tube 312. Since the hydrogen is continuously transported across the membrane, the dehydrogenation reaction is not slowed by a buildup of hydrogen pressure. Unreacted fuel exits the active reactor volume 421 through the recirculation outlet tube 311 and then is re-circulated back to the feedstock after condensing.

Hydrogen-selective Membranes

Membranes are thin, perm-selective materials that separate desired chemical species from a mixture of chemical species. Hydrogen-selective membranes are used in hydrogen reactors or devices to separate hydrogen from other gaseous mixtures that have potential to poison catalysts in fuel cells. For example, a palladium-alloy membrane is suitable for hydrogen separation from gas mixtures and is commonly used in hydrogenation and dehydrogenation reactions because palladium has a high selectivity for hydrogen. Various technologies may be used to prepare palladium membranes, including metal-organic chemical vapor deposition (MOCVD), sol-gel, electrolytic plating, electroless plating, and a combination of eletroless plating and electroplating. Electroless plating is generally preferred because it is a cheap, simple method and is applicable to material with complex shapes. The process is based on an autocatalytic reduction of metallic salt complexes on the surface of a support. The electroless plating of palladium is presented in the equation below, using hydrazine ($N_2H_4$) as the reducing agent.

$$2Pd(NH_3)_4^{2+} + N_2H_4 + 4OH^- \rightarrow 2Pd + 8NH_3 + N_2 + 4H_2O$$

Electroless plating parameters, such as temperature, pH, and types of reducing agent, directly affect the metal particle size deposited on the surface of the support, which in turn affects the membrane permeability and selectivity. The performance and the stability of the Pd membrane may also be increased by adding other metals such as Ag and Cu. Membrane performance is also related to the thickness of the deposited film. All these contributing factors may be appropriately tuned in order to produce a hydrogen-selective membrane with high hydrogen permeability and selectivity.

Although the present invention has been described in terms of particular implementations, it is not intended that the invention be limited to these implementations. Modifications will be apparent to those skilled in the art. For example, as disclosed above, the values of various process parameters, including temperature, pressures, concentrations, percentages, and other parameters, or other set of properties, including composition of the metal particles, choice of support material, experimental conditions, physical states and other properties can be changed to produce a variety of different hydrogen storage systems.

The foregoing description, for purposes of explanation, used specific nomenclature to provide a thorough understanding of the invention. However, it will be apparent to one skilled in the art that the specific details are not required in order to practice the invention. The foregoing descriptions of specific implementations of the present invention are presented for purpose of illustration and description. They are not intended to be exhaustive or to limit the invention to the precise forms disclosed. Many modifications and variations are possible in view of the above teachings. The implementations are shown and described in order to best explain the principles of the invention and its practical applications, to thereby enable others skilled in the art to best utilize the invention and various implementations with various modifications as are suited to the particular use contemplated. It is intended that the scope of the invention be defined by the following claims and their equivalents.

The invention claimed is:

1. A hydrogen-storage system comprising:
   an aliphatic-amine hydrogen carrier;
   a reactor, into which the aliphatic-amine hydrogen carrier is input, that includes a catalyst-containing reactor chamber and that outputs hydrogen gas and a nitrile dehydrogenated carrier; and
   a rehydrogenation subsystem that hydrogenates the nitrile dehydrogenated carrier to produce the aliphatic-amine hydrogen carrier.

2. The hydrogen-storage system of claim 1, wherein the aliphatic-amine hydrogen carrier is one or more of:
   ethylamine;
   propylamine;
   isopropylamine;
   butylamine;
   pentylamine;
   ethane-1,2-diamine;
   propane-1,3-diamine;
   butane-1,4-diamine;
   butane-1,3-diamine;
   pentane-1,3-diamine;
   pentane-1,5-diamine, and
   2-(aminomethyl) propane-1,3-diamine.

3. The hydrogen-storage system of claim 1, wherein the catalyst contained in the reactor chamber comprises one or more metal or metal oxide selected from among:
   rhodium;
   platinum;
   ruthenium;
   gold;
   palladium;
   cobalt;
   cobalt oxide;
   iron oxide;
   nickel oxide; and
   chromium oxide.

4. The hydrogen-storage system of claim 1, wherein the catalyst contained in the reactor chamber is dispersed on a gamma-alumina support material.

5. The hydrogen-storage system of claim 1, wherein the catalyst contained in the reactor chamber is dispersed on a metal-organic framework support material.

6. The hydrogen-storage system of claim 1, wherein the reactor is selected from among:
- a packed-bed reactor;
- a monolith reactor; and
- a flow-through hydrogen-membrane reactor.

7. The hydrogen-storage system of claim 6, wherein the flow-through hydrogen membrane-reactor further comprises:
- a reactor chamber that comprises a catalyst-containing membrane reactor tube and an outer chamber surrounding the membrane reactor tube ;
- an inlet that provides an input to the membrane reactor tube, through which the aliphatic-amine hydrogen carrier flows into the membrane reactor tube;
- a recirculation outlet that outputs unspent aliphatic-amine hydrogen carrier from the membrane reactor tube; and
- a hydrogen outlet that outputs hydrogen gas and the nitrile dehydrogenated carrier from the outer chamber.

8. The hydrogen-storage system of claim 7, wherein the membrane reactor tube has a wall composed of a hydrogen-selective membrane.

9. The hydrogen-storage system of claim 8, wherein the hydrogen-selective membrane is a palladium-alloy membrane.

10. The hydrogen-storage system of claim 7,
- wherein the membrane reactor tube is surrounded by heating elements to provide sufficient energy for catalytic dehydrogenation reactions;
- wherein the inlet and the recirculation outlet have a wall composed of an impermeable material; and
- wherein the inlet further comprises a gas port through which the aliphatic-amine hydrogen carrier enters the membrane reactor tube.

11. A method for storing hydrogen, the method comprising:
- providing an aliphatic-amine hydrogen carrier;
- supplying the aliphatic-amine hydrogen carrier to a reactor that includes a catalyst-containing reactor chamber and that produces hydrogen gas and a nitrile dehydrogenated carrier; and
- collecting and storing the nitrile dehydrogenated carrier for input to a rehydrogenation subsystem that hydrogenates the nitrile dehydrogenated carrier to produce the aliphatic-amine hydrogen carrier.

12. The method for storing hydrogen of claim 11, wherein the aliphatic-amine hydrogen carrier is one or more of:
- ethylamine;
- propylamine;
- isopropylamine;
- butylamine;
- pentylamine;
- ethane-1,2-diamine;
- propane-1,3-diamine;
- butane-1,4-diamine;
- butane-1,3-diamine;
- pentane-1,3-diamine;
- pentane-1,5-diamine; and
- 2-(aminomethyl) propane-1,3-diamine.

13. The method for storing hydrogen of claim 11, wherein the catalyst contained in the reactor chamber comprises one or more metal or metal oxide selected from among:
- rhodium;
- platinum;
- ruthenium;
- gold;
- palladium;
- cobalt;
- cobalt oxide;
- iron oxide;
- nickel oxide; and
- chromium oxide.

14. The method for storing hydrogen of claim 11, wherein the catalyst contained in the reactor chamber is dispersed on a gamma-alumina support material.

15. The method for storing hydrogen of claim 11, wherein the catalyst contained in the reactor chamber is dispersed on a metal-organic framework support material.

16. The method for storing hydrogen of claim 11, wherein the reactor is selected from among:
- a packed-bed reactor;
- a monolith reactor; and
- a flow-through hydrogen-membrane reactor.

17. The method for storing hydrogen of claim 16, wherein the flow-through hydrogen membrane-reactor further comprises:
- a reactor chamber that comprises a catalyst-containing membrane reactor tube and an outer chamber surrounding the membrane reactor tube;
- an inlet that provides an input to the membrane reactor tube, through which the aliphatic-amine hydrogen carrier flows into the membrane reactor tube;
- a recirculation outlet that outputs unspent aliphatic-amine hydrogen carrier from the membrane reactor tube; and
- a hydrogen outlet that outputs hydrogen gas and the nitrile dehydrogenated carrier from the outer chamber.

18. The method for storing hydrogen of claim 17, wherein the membrane reactor tube has a wall composed of a hydrogen-selective membrane.

19. The method for storing hydrogen of claim 18, wherein the hydrogen-selective membrane is a palladium-alloy membrane.

20. The method for storing hydrogen of claim 17,
- wherein the membrane reactor tube is surrounded by heating elements to provide sufficient energy for catalytic dehydrogenation reactions;
- wherein the inlet and the recirculation outlet have a wall composed of an impermeable material; and
- wherein the inlet further comprises a gas port through which the aliphatic-amine hydrogen carrier enters the membrane reactor tube.

* * * * *